United States Patent [19]

Barberet et al.

[11] Patent Number: Plant 6,056

[45] Date of Patent: Dec. 8, 1987

[54] CARNATION NAMED LONDRENAS

[75] Inventors: Nicole Barberet; Yves Ducloux, both of Antibes, France

[73] Assignee: Laboratoire de Physiologie Vegetale de La Londe, La Londe, France

[21] Appl. No.: 812,357

[22] Filed: Dec. 23, 1985

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler; John B. Lungmus

[57] ABSTRACT

A new variety of carnation plant distinguished by its recurrent and profuse production of medium sized, all white flowers during spring, midseason and fall, borne singly on erect and rather rigid flower stems of medium length, and having a vigorous and upright growth habit reaching a height of about 82 cm. at eight months.

1 Drawing Figure

BACKGROUND OF THE INVENTION

This new carnation cultivar originated as a seedling produced by us in the course of our breeding efforts carried on at La Londe, Les-Maures, VAR., France, with the object of producing new plants having blooms of a nice color and good growth qualities and resistant to *Fusarium oxysporum.* This new seedling resulted from our crossing selected plant varieties maintained in our collection of breeding plants at La Londe and this new seedling was selected by us because it appeared to have the plant qualities that we were seeking for a very good variety that would have favorable commercial attractiveness. Propagation of this selected seedling was carried on by us and under our direction at La Londe by means of cuttings with favorable results. Continued propagation in the same manner and by In Vitro propagation through several generations demonstrated that the novel characteristics of the original seedling were fully retained from generation to generation and appeared to be firmly fixed.

DESCRIPTION OF THE DRAWING

Our new variety of carnation is illustrated by the accompanying photographic drawing which shows a group of the flowers in various stages of opening from the bud near its first break to a fully opened flower, the color rendition being as nearly true as it is reasonably possible to obtain by conventional commercial photographic procedures.

DESCRIPTION OF THE NEW PLANT

The following is a description of our new variety of carnation plant as observed on plants grown in the southern part of France during the spring of 1985, the color designations being according to The R.H.S. Colour Chart published by The Royal Horticultural Society of London, England.

THE PLANT

Origin: Seedling.

Parentage:

*Seed parent.*—An unnamed and unpatented variety No. 79 C 6.

*Pollen parent.*—An unnamed and unpatented variety No. 8542 R. These plants were selected from our collection of breeding varieties maintained by us at our laboratory at La Londe, Les-Maures, VAR., France, for breeding purposes and each of these plants is fully identified in our permanent records maintained in our laboratory.

Classification:

*Botanic.—Dianthus caryophyllus.*

*Commercial.*—Spray carnation.

Form: Bush with at least four stems emitted near the ground.

Height: In average, about 82 cm. at eight months of growth.

Main stem:

*Length.*—Less than 15 cm. due to pinching.

Growth of flowering stems: Vigorous, upright and rather rigid.

Branching character: This plant produces few branches.

Foliage:

*Quantity.*—Not very abundant.

*Number of leaves.*—More than 120 at the seventh node.

*Size of leaf.*—About 18.6 cm. long and about 1.2 cm. wide.

*Shape.*—Linear, with a rolled margin and acuminate apex.

*Texture.*—Leathery.

*Ribs and veins.*—Hardly noticeable.

*Rachis.13* Hardly noticeable.

*Color.*—Upper side — RHS 189A. Under side — RHS 189A.

THE BUD

Form: Ovoid.

Size: Medium.

*Diameter.*—About 2.3 cm.

*Length.*—About 2.5 cm.

Opening rate: Normal.

Color:

*When sepals first divide.*—White.

*When sepals begin to unfurl.*—The same as in full bloom.

Sepals:

*Number.*—Five.

*Shape.*—Wide and joined together at the calyx and having a cuspidate apex. The sepals are hooded over the bud until the bud begins to break. The sepals stand up when the flowers open.

*Color.*—Inside — RHS 145D. Outside — RHS 144C and RHS 137D.

*Striae.*—The striae extends longitudinally of the sepal blade.

Calyx:

*Shape.*—Funnel shaped.

*Size.*—Medium in both breadth and length.

*Splitting.*—The calyx rarely splits.

*Aspect.*—Smooth.

Flower stem:

*Length.*—About 56 cm.

*Character.*—Erect and rather rigid.

*Color.*—RHS 189A.

THE FLOWER

Blooming habit: Recurrent, blooming profusely in spring, midseason and fall with a tendency to give fewer blooms in the fall.

Size: Medium.

*Diameter.*—About 8 cm. in average.

*Depth.*—About 7 cm. in average.

Borne: Singly.

Shape: When bloom first opens high centered and becoming flat when bloom matures.

Petalage:

*Number.*—About 66 in average.

*Arrangement.*—Imbricated.

*Form.*—Semi-circular in outline with finely serrated outer end edge.

*Texture.*—Soft.

*Appearance.*—Satiny.

*Color.*—Outer petals: Top side: Body — RHS 155B. Base — of greenish tint. Reverse side — RHS 155B. Inside petals: Top side: Body — RHS 155B. Base — Greenish tint. Reverse side — RHS 155B.

Petaloids:

*Number.*—Less than 10.

*Size.*—Smaller than petals.

*Color.*—The same as the petals.

Flower stem:

*Length.*—About 56 cm.

*Color.*—RHS 189A, cut at tenth node.

*Character.*—Upright and of good strength.

Discoloration after full bloom: None.

Effect of wet or hot weather: None.

Persistence: The flower petals hang on and dry.

Fragrance: Perceptible.

Disease resistance: Resistance to *Fusarium oxysporum* as observed INRA-Antibes-06600-France.

Lasting quality:

*As cut flower.*—At least ten days in vase keeping.

REPRODUCTIVE ORGANS

Stamens:

*Number.*—3 to 10 arranged around the ovary.

Anthers:

*Size.*—Less than 4 mm.

Filaments:

*Length.*—About 1 cm. in average.

*Color.*—Whitish.

Pistils:

*Number.*—3 to 4.

Styles:

*Length.*—3 cm. in average.

*Color.*—Whitish.

Stigmas:

*Color.*—Whitish.

Character of ovaries: Lightly ribbed.

This new plant most nearly resembles the variety "Londrioka" (U.S. Plant Pat. No. 5,419). Compared to "Londrioka", however, the color of "Londrenas" is somewhat less than pure white, the shape of the flower is flatter, and it is resistant to *Fusarium oxysporum.*

It should be noted that the foregoing characteristics of this plant can be more-or-less strongly modulated under the influence of environmental conditions (character of ground, latitude of growing area and method of cultivation).

We claim:

1. The new and distinct carnation cultivar, substantially as herein shown and described, characterized in particular by its well formed, medium sized blooms of white color which are produced profusely in a recurrent manner during the spring, midseason and fall seasons.

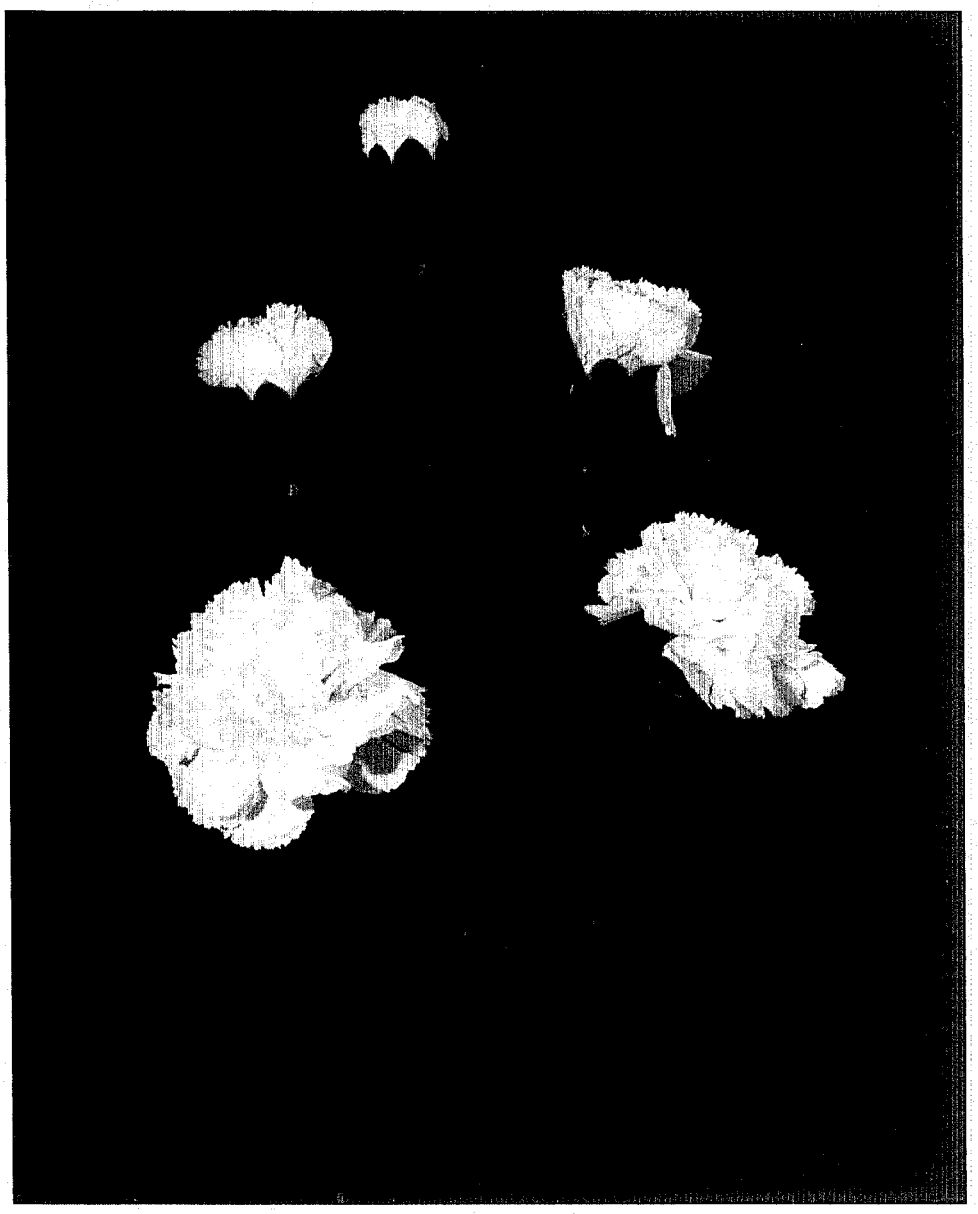

* * * * *